United States Patent [19]

Illian et al.

[11] Patent Number: 5,439,612

[45] Date of Patent: * Aug. 8, 1995

[54] CYCLOHEXYLPHENYLPYRIMIDINES, PROCESS FOR THEIR PREPARATION, AND THEIR USE IN LIQUID-CRYSTALLINE MIXTURES

[75] Inventors: Gerd Illian, Frankfurt am Main; Rainer Wingen, Hattersheim am Main; Ingrid Müller, Niedernhausen, all of Germany

[73] Assignee: Hoechst Aktiengesellschaft, Frankfurt am Main, Germany

[*] Notice: The portion of the term of this patent subsequent to Apr. 6, 2010 has been disclaimed.

[21] Appl. No.: 932,065

[22] Filed: Aug. 19, 1992

Related U.S. Application Data

[62] Division of Ser. No. 765,551, Sep. 25, 1991, Pat. No. 5,200,521.

[30] Foreign Application Priority Data

Sep. 27, 1990 [DE] Germany ............... 40 30 579.1

[51] Int. Cl.$^6$ ............ C09K 19/34; G02F 1/13
[52] U.S. Cl. ............... 252/299.61; 359/104; 252/299.63
[58] Field of Search ........... 252/299.01, 299.61, 252/299.63; 544/298, 335; 359/104

[56] References Cited

U.S. PATENT DOCUMENTS

| | | | |
|---|---|---|---|
| 4,698,176 | 10/1987 | Gray et al. ............ | 544/298 |
| 4,709,030 | 11/1987 | Petrzilka et al. .......... | 544/298 |
| 4,812,258 | 3/1989 | Krause et al. ............ | 524/298 |
| 4,879,144 | 11/1989 | Nakura et al. ............ | 428/1 |

(List continued on next page.)

FOREIGN PATENT DOCUMENTS

| | | |
|---|---|---|
| 0104011 | 3/1984 | European Pat. Off. |
| 0256670 | 2/1988 | European Pat. Off. |
| 0285395 | 10/1988 | European Pat. Off. |
| 0289270 | 11/1988 | European Pat. Off. |

(List continued on next page.)

OTHER PUBLICATIONS

Shobara et al., Chemical Abstracts, vol. 113, No. 26 (Dec. 26, 1990), Abstract No. 241609n.

(List continued on next page.)

*Primary Examiner*—Shean Wu
*Attorney, Agent, or Firm*—Curtis, Morris & Safford

[57] ABSTRACT

Cyclohexylphenylpyrimidines of the formula (I)

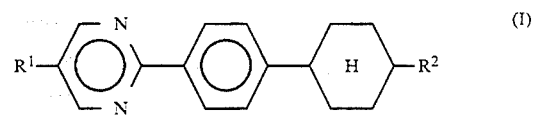

in which $R^1$ is straight-chain or branched, chiral or achiral alkyl or alkenyl having 2 to 16 carbon atoms, in which one or two nonadjacent —$CH_2$— groups may be replaced by —O—, —S—, —CO—, —COO—, —OCO—, —Si$(CH_3)_2$— or —C$(CH_3)_2$—, and in which one or more hydrogen atoms of the alkyl or alkenyl radical may be replaced by fluorine atoms, and in which the terminal $CH_3$ group of the alkyl may also be replaced by

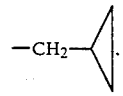

$R^2$ is straight-chain or branched, chiral or achiral alkyl having 1 to 10 carbon atoms, are particularly suitable components for ferroelectric liquid-crystal mixtures since they result in favorable properties, such as, for example, high contrast, when used in electrooptical switching and display devices.

11 Claims, No Drawings

U.S. PATENT DOCUMENTS

| | | | |
|---|---|---|---|
| 4,900,472 | 2/1990 | Miyazawa et al. | 544/335 |
| 4,906,400 | 3/1990 | Saito et al. | 544/298 |
| 4,911,863 | 3/1990 | Sage et al. | 544/335 |
| 4,917,818 | 4/1990 | Sawada et al. | 252/299.61 |
| 5,013,475 | 5/1991 | Shibata et al. | 544/325 |
| 5,034,152 | 7/1991 | Katagiri et al. | 252/299.65 |
| 5,047,170 | 9/1991 | Huynh-ba et al. | 252/299.6 |
| 5,075,031 | 12/1991 | Nohira et al. | 544/335 |
| 5,200,521 | 6/1993 | Illian et al. | 252/299.61 |

FOREIGN PATENT DOCUMENTS

| | | |
|---|---|---|
| 0316181 | 5/1989 | European Pat. Off. |
| 0318423 | 5/1989 | European Pat. Off. |
| 0343487 | 11/1989 | European Pat. Off. |
| 60-51778 | 3/1985 | Japan |
| 3156752 | 6/1988 | Japan |
| 1019072 | 1/1989 | Japan |
| 1031740 | 2/1989 | Japan |
| 1275568 | 11/1989 | Japan |
| 1316367 | 12/1989 | Japan |
| 2118618 | 5/1990 | Japan |
| WO87/07890 | 12/1987 | WIPO |

OTHER PUBLICATIONS

Uchida et al., CA 115-291378y (1991).
Mori et al., CA 115-82783n (1991).
Leclercq et al., CA 114-228228p (1991).
Sawada et al., CA 114-14998r (1991).
Toyne et al. CA 113-163266g (1990).
Obikawa, CA 113-49969p (1990).
Poetsch et al., CA 112-88951a (1989).
Huynh-Ba et al., CA 111-106356w (1989).
Ichimura et al., CA 111-105941w (1989).
Sawada et al., CA 111-105940v (1989).
Sawada et al., CA 110-240337y (1989).
Hopf et al., CA 107-49772v (1987).
Hopf et al., CA 107-15702g (1987).
Kitano et al., CA 105-162377s (1986).
Sawada et al., CA 104-139439j (1985).
CA 103-151043n (1985).

CYCLOHEXYLPHENYLPYRIMIDINES, PROCESS FOR THEIR PREPARATION, AND THEIR USE IN LIQUID-CRYSTALLINE MIXTURES

This application is a division of application Ser. No. 07/765,551, filed Sep. 25, 1991, now U.S. Pat. No. 5,200,521, issued Apr. 6, 1993.

BACKGROUND OF THE INVENTION

The unusual combination of anisotropic and fluid behavior of liquid crystals has resulted in their use in electrooptical switching and display devices, where their electrical, magnetic, elastic and/or thermal properties can be used to cause changes in alignment. Optical effects can be achieved, for example, using birefringence, the inclusion of dye molecules which absorb dichroically ("guest-host mode") or light scattering.

There has recently been increasing interest in, in particular, ferroelectric liquid crystals as a display medium in electrooptical components (displays) (for example Lagerwall et al., "Ferroelectric Liquid Crystals for Displays", SID Symposium, October Meeting 1985, San Diego, Calif. USA).

Practical use of ferroelectric liquid crystals in electrooptical displays requires chiral, tilted, smectic phases, such as $S_C$ phases [R. B. Meyer, L. Liebert, L. Strzelecki and P. Keller, J. Physique 36, L-69 (1975)], which are stable over a broad temperature range. This aim can be achieved using compounds which themselves form such phases, for example $S_c^*$ phases, or by doping compounds which form nonchiral, tilted, smectic phases with optically active compounds [M. Brunet, C. Williams, Ann. Phys. 3, 237, (1978)].

Furthermore, use of ferroelectric liquid-crystal mixtures in electrooptical components requires a uniform planar alignment of the liquid crystals in order to achieve high contrast. It has been shown that a uniform planar alignment in the $S_c$ phase can be achieved if the phase sequence of the liquid-crystal mixture with decreasing temperature is: isotropic→nematic→smectic A→smectic C (see, for example, K. Flatischler et al., Mol. Cryst. Liq. Cryst. 131, 21 (1985); T. Matsumoto et al., p. 468–470, Proc. of the 6th Int. Display Research Conf., Japan Display, 30 September-2 October 1986, Tokyo, Japan; M. Murakami et al., ibid., p. 344–347).

For ferroelectric (chiral smectic) liquid-crystal mixtures, the pitch of the helix must additionally be large, i.e. greater than 5 μm, in the $S_c^*$ phase and very large, i.e. greater than 10 μm or infinite, in the N* phase.

The optical response time, τ[μs] of ferroelectric liquid-crystal systems, which should be as short as possible, depends on the rotational viscosity of the system γγ[mPas], the spontaneous polarization $P_s$[nC/cm²] and the electrical field strength E[V/m] in accordance with the equation $$\tau \approx \frac{\gamma}{P_s \cdot E}$$

Since the field strength E is determined by the distance between the electrodes in the electrooptical component and by the applied voltage, the ferroelectric display medium must be of low viscosity and have high spontaneous polarization so that a short response time is achieved.

Finally, in addition to thermal, chemical and photochemical stability, a low optical anisotropy Δn, preferably <0.13, and a low positive or preferably negative dielectric anisotropy Δε are required (see S. T. Lagerwall et al., "Ferroelectric Liquid Crystals for Displays", SID Symposium, Oct. Meeting 1985, San Diego, Calif. USA).

All these requirements can only be achieved together by means of mixtures comprising a plurality of components. The base (or matrix) used preferably comprises compounds which if possible already have the desired phase sequence I→N→$S_A$→$S_C$. Further components of the mixture are frequently added to reduce the melting point and to broaden the $S_C$ and usually also the N phase, to induce optical activity, for pitch compensation and for matching the optical and dielectric anisotropies, but the rotational viscosity, for example, should not be increased if possible. It has become apparent that the use of mixture components which contain only two aromatic rings results in a low viscosity of the mixture.

Some of these components individually and also certain mixtures have already been disclosed in the prior art. However, since development, in particular of ferroelectric liquid-crystal mixtures, can in no way be regarded as complete, the manufacturers of displays are interested in various mixtures, also because, inter alia, conclusions on the quality of the liquid-crystalline mixtures too can only be achieved through the interaction of the liquid-crystalline mixtures with the individual components of the display devices or the cells (for example the alignment layer).

It is known that certain derivatives of phenylpyrimidine, in particular 5-alkyl-2-(4-alkoxyphenyl)pyrimidines, are able to form $S_c$, $S_A$ and N phases (see D. Demus and H. Zaschke, "Flüssige Kristalle in Tabellen" [Liquid Crystals in Tables], VEB Deutscher Verlag für Grundstoffindustrie, Leipzig 1974, pp. 260-261) and can also be converted into ferroelectric liquid-crystal mixtures through addition of optically active dopes [see L. M. Blinov et al., Sow. Phys. Usp. 27 (7), 492 (1984); L. A. Beresnew et al., Ferroelectrics, 59 [321]/1 (1984), presented at the 5th Conference of Soc. Countries on Liquid Crystals, Odessa, USSR, October 1983; DE-A 35 15 347, EP-A 0 206 228 and EP-A 0 225 195].

It is also known that relatively low melting points and a broadening of the desired liquid-crystalline phases can be achieved by mixing a plurality of liquid-crystalline compounds [see D. Demus etal., Mol. Cryst. Liq. Cryst. 25, 215 (1974), J. W. Goodby, Ferroelectrics 49, 275 (1983)], and that the melting point depression is the more pronounced the more the mixture components also differ structurally from one another (for example J. S. Dave et al., J. Chem. Soc. 1955, 4305). This also applies to the melting point depression in systems which have the phase sequence X⇌$S_c$⇌$S_A$⇌N⇌I, which is ideal for the production of electrooptical components. In this case, however, other essential characteristic quantities tend to be retained only if the components of the mixture are structurally similar and themselves have this phase sequence. The two objects—melting point depression and shift in the lower temperature limit of the $S_c$ phase toward lower temperature on the one hand and substantial retention of their other characteristic quantities on the other hand—are thus contradictory.

It has already been stated that liquid crystals having a terminal cyclopropyl group (see DE-A 3 915 804 and DE-A 3 839 330) and liquid crystals having a geminal dimethyl substitution (see DE-A 4 003 012) or having a dimethylsilyl substitution (see DE-A 3 827 600) in the chain are suitable for use in liquid-crystalline mixtures.

However, the dimethyl-branched compounds have comparatively narrow hemtic phase ranges. This is particularly true for compounds having only two aromatic rings, which, due to their low viscosity, are preferred over compounds having three aromatic rings. However, the compounds having two aromatic rings which are presented in DE-A 4 003 012 and DE-A 3 827 600 either have no hemtic or no $S_A$ phase and/or relatively high melting points and unsatisfactory melting point properties in mixtures.

Also in the case of the substances having two aromatic rings which are presented in DE-A 3 915 804, the examples having the highest clearing points have no $S_A$ phase. Although the use of these components in mixtures frequently results in an increase in the temperature of the nematic and $S_c$ phases, it also results in the disappearance of the $S_A$ phase.

SUMMARY OF THE INVENTION

It has now been found that specific tricyclic compounds achieve the object set at the outset—assurance of a low melting point and broad liquid-crystalline phases with simultaneous retention of favorable electrooptical properties in mixtures (response times, viscosities, switching angle). The invention relates to a cyclohexylphenylpyrimidine of the formula (I)

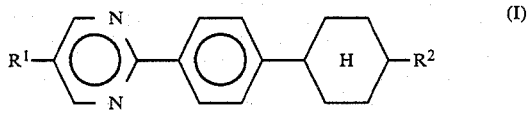

in which:
R$^1$ is straight-chain or branched, chiral or achiral alkyl or alkenyl having 2 to 16 carbon atoms, in which one or two nonadjacent —CH$_2$— groups may be replaced by —O—, —S—, —CO—, —COO—, —OCO—, —Si(CH$_3$)$_2$— or —C(CH$_3$)$_2$—, and in which one or more hydrogen atoms of the alkyl or alkenyl radical may also be replaced by fluorine atoms, and in which the terminal CH$_3$ group of the alkyl may also be replaced by

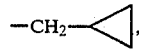

R$^2$ is straight-chain or branched, chiral or achiral alkyl having 1 to 10 carbon atoms.

DESCRIPTION OF THE PREFERRED EMBODIMENTS

Preference is given to a cyclohexylphenylpyrimidine of the abovementioned formula (I), in which
R$^1$ is straight-chain or branched, chiral or achiral alkyl having 2 to 16 carbon atoms in which one —CH$_2$— group has been replaced by —C(CH$_3$)$_2$— or —Si(CH$_3$)$_2$— and in which a —CH$_2$— group which is nonadjacent thereto may be replaced by —O—, —S—, —COO— or —OCO—.
Preference is likewise given to a cyclohexylphenylpyrimidine
in which R$^1$ is straight-chain or branched, chiral or achiral alkyl having 2 to 16 carbon atoms in which the terminal CH$_3$ group has been replaced by

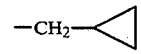

and in which one —CH$_2$— group may be replaced by —O—, —S—, —COO— or —O—CO—.
R$^1$ is also preferably straight-chain alkyl having 4 to 12 carbon atoms in which one —CH$_2$— group may be replaced by —O— or —S—.
In a further embodiment of the invention,
R$^1$ is straight-chain alkyl having 4 to 12 carbon atoms in which one —CH$_2$— group has been replaced by —C(CH$_3$)$_2$— and a further —CH$_2$— group which is nonadjacent thereto may be replaced by —O—, or
R$^1$ is straight-chain alkyl having 4 to 12 carbon atoms in which the terminal CH$_3$ group has been substituted by

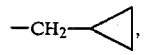

and
R$^2$ is preferably straight-chain alkyl having 2 to 8 carbon atoms.

The said object is also achieved by a liquid-crystalline mixture, in particular a ferroelectric liquid-crystalline mixture, which contains at least one compound of the formula (I).

The liquid-crystal mixtures generally comprise at least 2, preferably 2 to 20, particularly preferably 2 to 15, components, including at least one of the compounds claimed according to the invention. The other constituents are preferably selected from known compounds having nematic, cholesteric and/or tilted smectic phases, including, for example, Schiff's bases, biphenyls, terphenyls, phenylcyclohexanes, cyclohexylbiphenyls, pyrimidines, cinnamic acid esters, cholesterol esters and various bridged, polycyclic esters of p-alkylbenzoic acids which have terminal polar groups. In general, the commercially available liquid-crystal mixtures are, even before addition of the compound(s) according to the invention, in the form of mixtures of various components, of which at least one is mesogenic, i.e. has a liquid-crystal phase as the compound, in derivatized form or mixed with certain components [gives rise to expectations of at least one enantiotropic (clearing point < melting point) or monotropic (clearing point > melting point) mesophase formation].

The liquid-crystal mixtures generally contain from 0.1 to 70 mol-%, preferably from 0.5 to 50 mol-%, in particular from 1 to 25 mol-%, of the cyclohexylphenylpyrimidine(s) according to the invention.

Preference is given to mixtures which contain 5-alkoxy-2-(4-alkoxyphenyl)pyrimidines, 5-alkyl-2-(4-alkoxyphenyl)pyrimidines or corresponding phenylpyrimidines, in which an alkyl radical may be substituted by a terminal cyclopropyl, in addition to at least one compound according to the invention.

The values for spontaneous polarization P$_s$[nC/cm$^2$], contrast C and optical response time $\tau$[μs] are measured for the ready-to-use ferroelectric liquid crystal mixtures, with all measurements being carried out at a temperature of 25° C.

The $P_s$ values are measured by the method of H. Diamant et al. (Rev. Sci. Instr., 28, 30, 1957), using measurement cells having an electrode separation of 2 µm and rubbed polyimide as the alignment layer. In order to determine $\tau$ and C, the measurement cell is clamped on the rotating stage of a polarizing microscope between crossed analyzer and polarizer. In order to determine the contrast (C), the measurement cell is positioned by rotating in such a manner that a photodiode indicates minimum light transmission (dark state). The microscope illumination is adjusted so that the photodiode indicates the same light intensity for all cells. After a switching operation, the light intensity changes (bright state) and the contrast is calculated from the ratio of the light intensities in these states.

The response time $\tau$ is determined using a photodiode by measuring the time taken for the light signal to rise from a signal height of 10 to 90%. The switching voltage comprises rectangular pulses and is ±10 V/µm.

The phase-transition temperatures are determined from changes in texture using a polarizing microscope while heating. By contrast, the melting point was determined using a DSC instrument. The phase-transition temperatures between the phases nematic (N or N*)
smectic C ($S_c$ or $S_c$*)
smectic A ($S_A$ or $S_A$*)
crystalline (X)

are indicated in °C. and the values are in sequence between the phase codes.

The mixtures according to the invention can advantageously be employed as components in ferroelectric liquid-crystal switching and display devices. These devices generally contain outer plates, electrodes, at least one polarizer, alignment layers and a liquid-crystalline medium. For details, reference is made to the literature cited at the outset.

The compounds according to the invention can be prepared by methods which are known per se from the literature. Thus, for example, cyclization reactions, as described in Zaschke et al., J. Prakt. Chem. 312, 494 (1970), can be used to build up the pyrimidine unit (schemes 1 and 2).

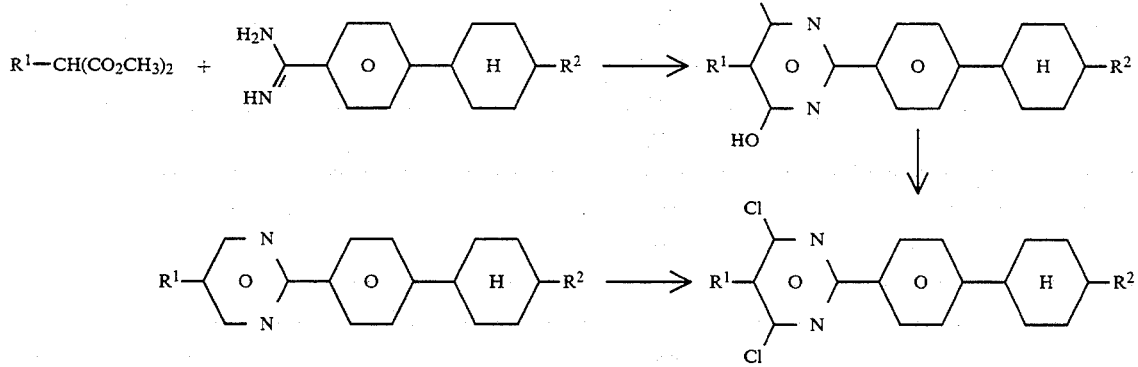

Scheme 1

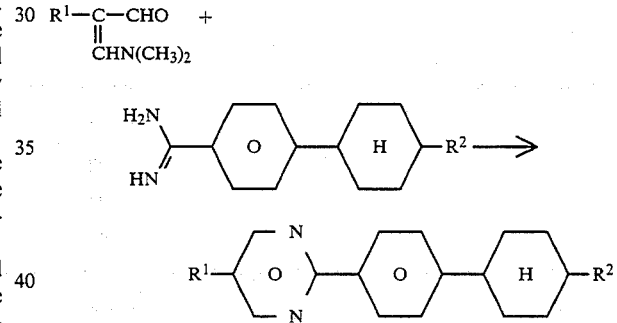

Scheme 2

It is also possible to link a pyrimidine derivative containing halogen substituents on the phenyl and built up in accordance with scheme 1 or 2 to a cyclohexane fragment via organometallic intermediates.

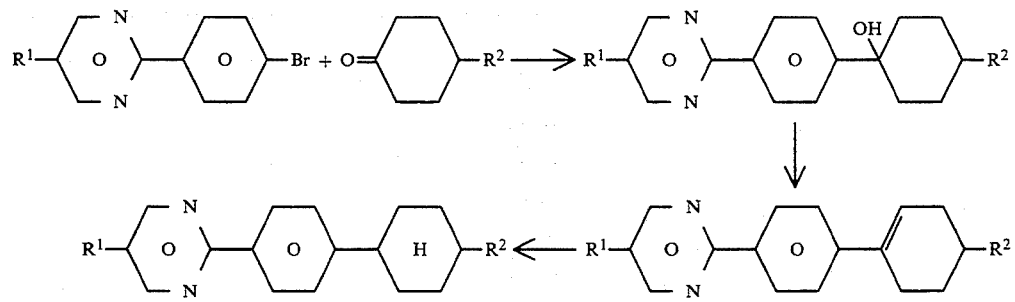

Scheme 3

Finally, it is also possible to carry out the organometallic coupling as shown in scheme 4 between a pyrimidine fragment and a cyclohexyl fragment.

Scheme 4

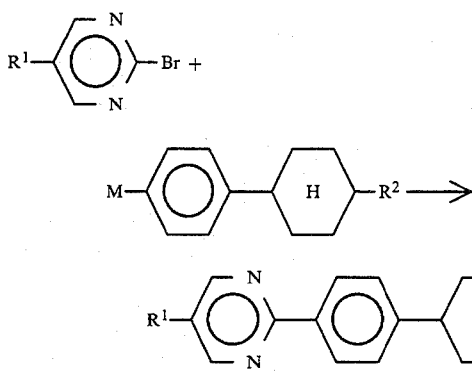

The liquid-crystal mixtures described can advantageously be employed in electrooptical switching and display devices (FLC light valves or displays). These have, inter alia, the following constituents: a liquid-crystalline mixture according to the invention (containing a cyclohexylphenylpyrimidine), outer plates (for example made of glass or plastic), coated with transparent electrodes (two electrodes), at least one alignment layer, spacers, sealing frame, polarizers and, for color displays, thin colored filter layers. Further possible components are antireflexion, passivation, compensation and barrier layers and electrically nonlinear elements, such as, for example, thin-film transistors (TFTS) and metal-insulator-metal (MIM) elements. The general structure of liquid-crystal displays has already been described in detail in the relevant monographs (for example E. Kaneko, "Liquid Crystal TV Displays: Principles and Applications of Liquid Crystal Displays", KTK Scientific Publishers, 1987, pages 12–30 and 163–172).

The invention is described in greater detail by means of the examples below:

Example 1

Synthesis of 5-(8-cyclopropyloctyloxy)-2-(4″-trans-pentylcyclohexyl-4-phenyl)pyrimidine

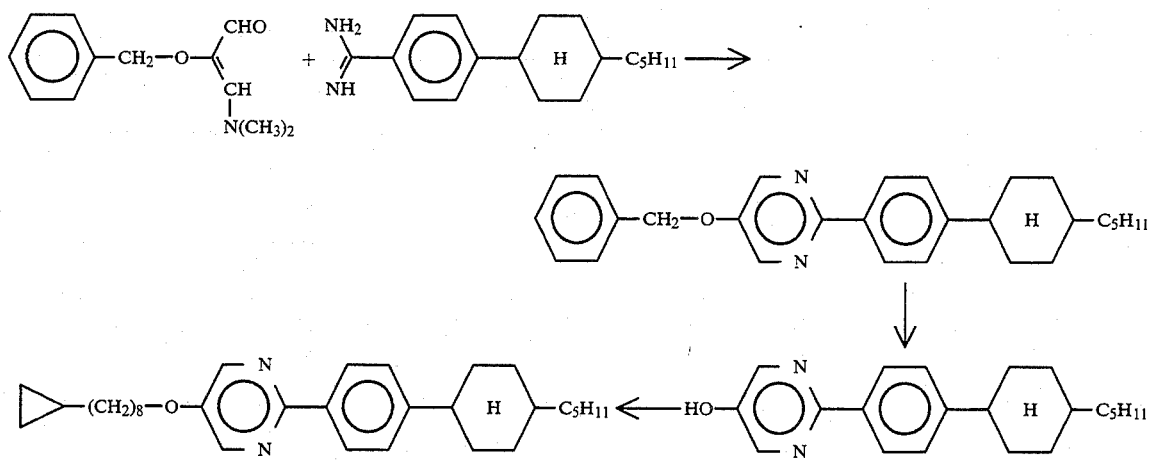

A solution of 1.94 g of 5-hydroxy-2-[4-(4-trans-pentylcyclohexyl)phenyl]pyrimidine, obtained by condensation of 2-benzyloxy-3-dimethylaminoacrolein with 4-(4-trans-pentylcyclohexyl)benzamidine and subsequent removal ($H_2Pd/THF$) of the benzyl protecting group of the 5-benzyloxy-2-[4-(4-trans-pentylcyclohexyl)phenyl]pyrimidine initially formed, in 50 ml of dimethylformamide is treated with 0.36 g of sodium hydride (60%). When the reaction thus subsided, 2.1 g of 8-cyclopropyloctyl bromide are added, and the mixture is stirred for 3 hours at a temperature of 60° C. Hydrolysis and extraction with dichloromethane gives 3.2 g of crude product; purification is carried out by chromatography ($SiO_2/CH_2Cl_2$) and recrystallization from n-hexane.

Use Example 1 a) A mixture comprises the components

| | |
|---|---|
| 5-octyloxy-2-(4-hexyloxyphenyl)pyrimidine | 23.8 mol-% |
| 5-octyloxy-2-(4-octyloxyphenyl)pyrimidine | 11 mol-% |
| 5-octyloxy-2-(4-butyloxyphenyl)pyrimidine | 25.2 mol-% |
| 5-octyloxy-2-(4-decyloxyphenyl)pyrimidine | 20 mol-% |
| 5-(8-cyclopropyloctyloxy)-2-(4″-trans-propylcyclohexyl-4′-phenyl)pyrimidine | 20 mol-% | and has the following liquid-crystalline phase ranges:

X 11 $S_c$ 85 $S_A$ 99.5 N 109 I b) By comparison, the liquid-crystalline mixture described in DE-A 38 31 226, which only differs from the abovementioned mixture in that it contains no cyclohexylphenylpyrimidine component, has the following phase ranges:

X 13 $S_c$ 81 $S_A$ 95 N 98 I

Addition of the compound according to the invention results in a depression of the melting point and an increase in the liquid-crystalline phase ranges.

Use Example 2 a) A mixture comprises the components

| | |
|---|---|
| 5-octyloxy-2-(4-hexyloxyphenyl)pyrimidine | 23.8 mol-% |
| 5-octyloxy-2-(4-octyloxyphenyl)pyrimidine | 11 mol-% |
| 5-octyloxy-2-(4-butyloxyphenyl)pyrimidine | 25.2 mol-% |
| 5-octyloxy-2-(4-decyloxyphenyl)pyrimidine | 20 mol-% |
| 5-(8-cyclopropyloctyloxy)-2-(4″-trans-pentylcyclohexyl-4′-phenyl)pyrimidine | 20 mol-% | and has the following liquid-crystalline phase ranges:

X 11 $S_c$ 83.5 $S_A$ 100N 110 I b) By comparison, a liquid-crystalline mixture described in DE-A 38 31 226, which only differs from the above-mentioned mixture in that it contains no cyclohexylphenylpyrimidine component, has the following phase ranges:

X 13 $S_c$ 81 $S_A$ 95N 98 I

Addition of the compound according to the invention results in a depression of the melting point and an increase in the liquid-crystalline phase ranges. Use Example 3 a) A mixture comprising the components

| | |
|---|---|
| 5-octyloxy-2-(4-hexyloxyphenyl)pyrimidine | 23.8 mol-% |
| 5-octyloxy-2-(4-octyloxyphenyl)pyrimidine | 11 mol-% |
| 5-octyloxy-2-(4-butyloxyphenyl)pyrimidine | 25.2 mol-% |
| 5-octyloxy-2-(4-decyloxyphenyl)pyrimidine | 20 mol-% |
| 5-(8-cyclopropyloctyloxy)-2-(4″-trans-propylcyclohexyl-4′-phenyl)pyrimidine | 16 mol-% |
| 5-(7,7-dimethylundecyloxy)-2-(4″-trans-propylcyclohexyl-4′-phenyl)pyrimidine | 4 mol-% | has the following liquid-crystalline phase ranges:

X 11 $S_c$ 84 $S_A$ 97N 108 I b) By comparison, the liquid-crystalline mixture described in DE-A 38 31 226, which only differs from the abovementioned mixture in that it contains no cyclohexylphenylpyrimidine component, has the following phase ranges:

X 13 $S_c$ 81 $S_A$ 95N 98 I

Addition of the compounds according to the invention results in a depression of the melting point and an increase in the liquid-crystalline phase ranges.

Use Example 4 a) A mixture comprising the components

| | |
|---|---|
| 5-octyloxy-2-(4-hexyloxyphenyl)pyrimidine | 23.8 mol-% |
| 5-octyloxy-2-(4-octyloxyphenyl)pyrimidine | 11 mol-% |
| 5-octyloxy-2-(4-butyloxyphenyl)pyrimidine | 25.2 mol-% |
| 5-octyloxy-2-(4-decyloxyphenyl)pyrimidine | 20 mol-% |
| 5-[4-(butyldimethylsilyl)butyloxy]-2-(4″-trans-pentylcyclohexyl-4′-phenyl)-pyrimidine | 20 mol-% | has the following liquid-crystalline phase ranges:

X 9 $S_c$ 77 $S_A$ 81N 97 I b) By comparison, the liquid-crystalline mixture described in DE-A 38 31 226, which only differs from the abovementioned mixture in that it contains no cyclohexylphenylpyrimidine component, has the following phase ranges:

X 13 $S_c$ 81 $S_A$ 95N 98 I

Addition of the compound according to the invention results in a depression of the melting point and an increase in the liquid-crystalline phase ranges.

Use Example 5 a) A mixture comprising the components

| | |
|---|---|
| 5-octyl-2-(4-hexyloxyphenyl)pyrimidine | 20.5 mol-% |
| 5-octyl-2-(4-octyloxyphenyl)pyrimidine | 13.6 mol-% |
| 5-octyl-2-(4-decyloxyphenyl)pyrimidine | 13.3 mol-% |
| 5-octyl-2-(4′-(6″-cyclopropylhexyloxy)-phenyl)pyridine | 16.6 mol-% |
| 5-octyl-2-(4′-(6″-cyclopropylhexylcarbonyloxyphenyl)pyrimidine | 16.0 mol-% |
| 5-(8-cyclopropyloctyloxy)-2-(4″-trans-propylcyclohexyl-4′-phenyl)-pyrimidine | 20.0 mol-% | has the following liquid-crystalline phase ranges:

X 10 $S_c$ 64 $S_A$ 73N 82 I b) By comparison, the liquid-crystalline mixture described in DE-A 38 31 226, which only differs from the abovementioned mixture in that it contains no cyclohexylphenylpyrimidine component, has the following phase ranges:

X −3 $S_c$ 50 $S_A$ 60N 62 I

Addition of the compound according to the invention results in a depression of the melting point and a broadening of the liquid-crystalline phase ranges. This example confirms that the compounds according to the invention are also suitable in mixtures which contain phenylpyridines in addition to phenylpyrimidines.

Use Example 6 a) A mixture comprising the components

| | |
|---|---|
| 5-octyloxy-2-(4-hexyloxyphenyl)pyrimidine | 11.4 mol-% |
| 5-octyloxy-2-(4-butyloxyphenyl)pyrimidine | 12.6 mol-% |
| 5-octyloxy-2-(4-decyloxyphenyl)pyrimidine | 6.9 mol-% |
| 5-octyloxy-2-(4-octyloxyphenyl)pyrimidine | 3.8 mol-% |
| 5-octyloxy-2-(4-dodecyloxyphenyl)pyrimidine | 6.9 mol-% |
| 5-octyl-2-(4-dodecyloxyphenyl)pyrimidine | 10.2 mol-% |
| 4′-(5-decylpyrimidin-2-yl)phenyl trans-4-pentylcyclohexanecarboxylate | 16.2 mol-% |
| 4-(5-octylpyrimidin-2-yl)phenyl heptanoate | 17.0 mol-% |
| 5-(8-cyclopropyloctyloxy)-2-(4″-trans-propylcyclohexyl-4′-phenyl)pyrimidine | 15.0 mol-% | has the following liquid-crystalline phase ranges:

X −7 $S_c$ 78 $S_A$ 85N 105 I b) By comparison, the liquid-crystalline mixture described in DE-A 38 31 226, which only differs from the abovementioned mixture in that it contains no cyclohexylphenylpyrimidine component, has the following phase ranges:

X −4 $S_c$ 69 $S_A$ 80N 92 I

Addition of the compound according to the invention results in a depression of the melting point and an increase in the liquid-crystalline phase ranges.

Use Example 7 a) A mixture comprising the components

| | |
|---|---|
| 5-octyloxy-2-(4-hexyloxyphenyl)pyrimidine | 13.0 mol-% |
| 5-octyloxy-2-(4-butyloxyphenyl)pyrimidine | 14.5 mol-% |
| 5-octyloxy-2-(4-decyloxyphenyl)pyrimidine | 8 mol-% |

-continued

| | |
|---|---|
| 5-octyloxy-2-(4-octyloxyphenyl)pyrimidine | 4.4 mol-% |
| 5-octyl-2-(4-dodecyloxyphenyl)pyrimidine | 11.8 mol-% |
| 4'-(5-decylpyrimidin-2-yl)phenyl trans-4-pentylcyclohexanecarboxylate | 18.7 mol-% |
| 4-(5-octylpyrimidin-2-yl)phenyl heptanoate | 19.6 mol-% |
| 5-(8-cyclopropyloctyloxy)-2-(4''-trans-propylcyclohexyl-4'-phenyl)pyrimidine | 10 mol-% | has the following liquid-crystalline phase ranges:

X $-8$ $S_c$ 76 $S_A$ 80.5N 101 I b) By comparison, the liquid-crystalline mixture described in DE-A 38 31 226, which only differs from the abovementioned mixture in that it contains no cyclohexylphenylpyrimidine component, has the following phase ranges:

X $-7$ $S_c$ 73.5 $S_A$ 77N 96 I

Addition of the compound according to the invention results in a depression of the melting point and a significant increase in the liquid-crystalline phase ranges.

Use Example 8 a) A mixture comprising the components

| | |
|---|---|
| 5-octyl-2-(4-hexyloxyphenyl)pyrimidine | 31.2 mol-% |
| 5-octyl-2-(4-octyloxyphenyl)pyrimidine | 28.0 mol-% |
| 5-octyl-2-(4-decyloxyphenyl)pyrimidine | 20.8 mol-% |
| 5-(8-cyclopropyloctyloxy)-2-(4''-trans-propylcyclohexyl-4'-phenyl)pyrimidine | 20 mol-% | has the following liquid-crystalline phase ranges:

X 7 $S_c$ 62 $S_A$ 71N 87 I b) By comparison, the liquid-crystalline mixture described in DE-A 38 31 226, which only differs from the abovementioned mixture in that it contains no cyclohexylphenylpyrimidine component, has the following phase ranges:

X 17 $S_c$ 51 $S_A$ 60N 68 I

Addition of the compound according to the invention results in a depression of the melting point and a significant increase in the liquid-crystalline phase ranges.

c) A comparison mixture which contains the following component, which was claimed in DE-A 3915804, 4''-(5-(9'-cyclopropylnonyloxy)pyrimidin-2-yl)phenyl trans-4-pentylcyclohexanecarboxylate instead of the component according to the invention has the following liquid-crystalline phases:

X 36 $S_c$ 58N 90 I

This comparison substance likewise contains only two aromatic rings and differs from the substance in mixture 7a according to the invention essentially through the carboxyl group. This substance also increases the liquid-crystalline phase width in mixtures, but has the disadvantage that it increases the melting point of the mixture and suppresses the $S_A$ phase.

Use Example 9 a) A mixture comprising the components

| | |
|---|---|
| 5-octyl-2-(4-hexyloxyphenyl)pyrimidine | 25.9 mol-% |
| 5-octyl-2-(4-octyloxyphenyl)pyrimidine | 23.2 mol-% |
| 5-octyl-2-(4-decyloxyphenyl)pyrimidine | 17.3 mol-% |
| 5-(8-cyclopropyloctyloxy)-2-(4''-trans-propylcyclohexyl-4'-phenyl)pyrimidine | 13.6 mol-% |
| 5-[4-(butyldimethylsilyl)butyloxy]-2-(4''-trans-propylcyclohexyl-4'-phenyl)-pyrimidine | 20 mol-% | has the following liquid-crystalline phase ranges:

X $-2$ $S_c$ 55N 84 I b) By comparison, the liquid-crystalline mixture described in DE-A 38 31 226, which only differs from the abovementioned mixture in that it contains no cyclohexylphenylpyrimidine component, has the following phase ranges:

X 17 $S_c$ 51 $S_A$ 60N 68 I

Addition of the compounds according to the invention results in a significant depression of the melting point and an increase in the liquid-crystalline phase ranges.

Use Example 10 a) A mixture comprising the components

| | |
|---|---|
| 5-octyl-2-(4-hexyloxyphenyl)pyrimidine | 25.6 mol-% |
| 5-octyl-2-(4-octyloxyphenyl)pyrimidine | 23.0 mol-% |
| 5-octyl-2-(4-decyloxyphenyl)pyrimidine | 17.0 mol-% |
| 5-(8-cyclopropyloctyloxy)-2-(4''-trans-propylcyclohexyl-4'-phenyl)pyrimidine | 14.4 mol-% |
| 5-(7'7'-dimethylundecyloxy)-2-(4''-trans-propylcyclohexyl-4'-phenyl)pyrimidine | 20.0 mol-% | has the following liquid-crystalline phase ranges:

X 13 $S_c$ 67N 91 I b) By comparison, the liquid-crystalline mixture described in DE-A 38 31 226, which only differs from the abovementioned mixture in that it contains no cyclohexylphenylpyrimidine component, has the following phase ranges:

X 17 $S_c$ 51 $S_A$ 60N 68 I

Addition of the compound according to the invention results in a significant depression of the melting point and an increase in the liquid-crystalline phase ranges.

Use Example 11 a) A mixture comprising the components

| | |
|---|---|
| 5-octyl-2-(4-hexyloxyphenyl)pyrimidine | 27.3 mol-% |
| 5-octyl-2-(4-decyloxyphenyl)pyrimidine | 18.2 mol-% |
| 5-decyl-2-(4-hexyloxyphenyl)pyrimidine | 17.7 mol-% |
| 5-octyl-2-(4-heptylcarbonyloxyphenyl)-pyrimidine | 16.8 mol-% |
| 5-(8-cyclopropyloctyloxy)-2-(4''-trans-pentylcyclohexyl-4'-phenyl)pyrimidine | 20 mol-% | has the following liquid-crystalline phase ranges:

X $-1$ $S_c$ 61 $S_A$ 72N 84 I b) By comparison, the liquid-crystalline mixture, which only differs from the abovementioned mixture in that it contains no cyclohexylphenylpyrimidine component, has the following phase ranges:

X 8 $S_c$ 48 $S_A$ 61N 65 I

Addition of the compound according to the invention results in a significant depression of the melting point and an increase in the liquid-crystalline phase ranges. This example confirms that the substances according to the invention are suitable, in particular, in mixtures which predominantly comprise alkyl(alkoxyphenyl)-pyrimidines.

Use Example 12 a) A mixture comprising the components

| | |
|---|---|
| 5-octyl-2-(4-hexyloxyphenyl)pyrimidine | 24.1 mol-% |
| 5-octyl-2-(4-decyloxyphenyl)pyrimidine | 16.1 mol-% |
| 5-decyl-2-(4-hexyloxyphenyl)pyrimidine | 15.6 mol-% |
| 5-octyl-2-(4-heptylcarbonyloxyphenyl)-pyrimidine | 12.2 mol-% |
| 5-(8-cyclopropyloctyloxy)-2-(4''-trans-pentylcyclohexyl-4'-phenyl)pyrimidine | 16.0 mol-% |
| 5-(7'7'-dimethylundecyloxy)-2-(4''-trans-propylcyclohexyl-4'-phenyl)pyrimidine | 16.0 mol-% | has the following liquid-crystalline phase ranges:

X −6 $S_c$ 68 $S_A$ 72N 89 I b) By comparison, the liquid-crystalline mixture, which only differs from the abovementioned mixture in that it contains no cyclohexylphenylpyrimidine components, has the following phase ranges:

X 8 $S_c$ 48 $S_A$ 61N 65 I

Addition of the compounds according to the invention results in a significant depression of the melting point and an increase in the liquid-crystalline phase ranges. This example confirms that the substances according to the invention are suitable, in particular, in mixtures which predominantly comprise 5-alkoxy-2-(4-alkoxyphenyl)pyrimidines, 5-alkyl-2-(4-alkoxyphenyl)-pyrimidines or corresponding phenylpyridines and have liquid-crystalline phases which are too narrow for the user.

Use Example 13 a) A mixture comprises the components

| | |
|---|---|
| 5-octyl-2-(4-hexyloxyphenyl)pyrimidine | 34.6 mol-% |
| 5-octyl-2-(4-decyloxyphenyl)pyrimidine | 23.0 mol-% |
| 5-decyl-2-(4-hexyloxyphenyl)pyrimidine | 22.4 mol-% |
| 5-(8-cyclopropyloctyloxy)-2-(4''-trans-pentylcyclohexyl-4'-phenyl)pyrimidine | 20.0 mol-% | and has the following liquid-crystalline phase ranges:

X 8.5 $S_c$ 63 $S_A$ 75N 87 I b) By comparison, the liquid-crystalline mixture described in DE-A 38 31 226, which only differs from the abovementioned mixture in that it contains no cyclohexylphenylpyrimidine component, has the following phase ranges:

X 12 $S_c$ 47 $S_A$ 63N 67 I

Addition of the compound according to the invention results in a depression of the melting point and an increase in the liquid-crystalline phase ranges.

Use Example 14

A ferroelectric mixture comprises

| | |
|---|---|
| Example mixture 12 | 94.73 mol-% |
| (2S,3S)-2-[4-(5-octylpyrimidin-2-yl)-phenoxy]methyl-3-butyloxirane | 1.94 mol-% |
| (S)-4-(2-octyloxypyrimidin-5-yl)phenyl [spiro(1,3-dioxolane-2,1'-cyclohexane)-4-yl]methyl ether | 1.14 mol-% |
| 4-(2-octyloxypyrimidin-5-yl)phenyl (2R,3R)-3-propyloxirane-2-carboxylate | 2.19 mol-% | and has the following phases:

X −7 $S_c$ 67 $S_A$ 71N 87 I

This mixture has a polarization of 10 nC/cm$^2$ at 25° C. and switches with a response time of 113 μs in a 2 μm thick layer at a field strength of 10 Vμm$^{-1}$.

The tables below show the temperatures for phase transitions in °C. Monotropic phase transitions are indicated in parentheses.

Table 1

Example substances of the formula (II)

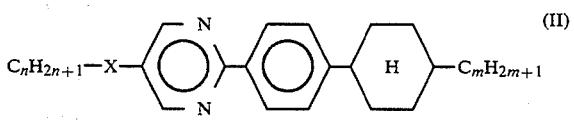

5-alkyl(oxy)-2-(4''-alkyl-trans-cyclohexane-4'-phenyl)-pyrimidines

| Example No. | Phase-transition temperatures* | | | | | | | |
|---|---|---|---|---|---|---|---|---|
| | n | x | m | X | $S_x$ | $S_c$ | $S_A$ | N | I |
| 1 | 8 | 0 | 5 | 65 | 83 | 119 | — | 181 |
| 2 | 8 | — | 5 | 74 | — | 88 | 103 | 158 |

Table 2

Example substances of the formula (III)

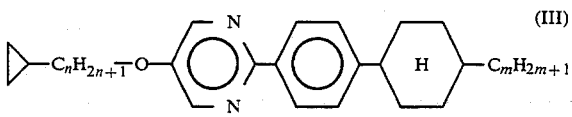

5-(cyclopropylalkoxy)-2-(4''-alkyl-trans-cyclohexane-4'-phenyl)pyrimidine

| Example No. | Phase-transition temperatures* | | | | | | |
|---|---|---|---|---|---|---|---|
| | n | m | X | $S_x$ | $S_c$ | $S_A$ | N | I |
| 3 | 4 | 5 | 81 | (75) | — | — | 180 |
| 4 | 6 | 5 | 63 | 93 | 100 | — | 173 |
| 5 | 8 | 5 | 75 | — | 122 | 135.5 | 264 |
| 6 | 6 | 3 | 80 | (70) | 84 | — | 174 |
| 7 | 8 | 3 | 86 | — | 111 | 123 | 165 |

It can be seen from the examples in Table 2 that the components containing the cyclopropylhexyloxy group are preferred since they have the lowest melting point in the homologous series. The compounds containing the cyclopropyloctyloxy group are particularly preferred since they contain the desired liquid-crystalline phases and no liquid-crystalline phase of higher order. Comparison of Example Compound 1 from Table 1 with the compound from Example 5 of Table 2 shows that the compounds which contain a cyclopropyl group in place of a $C_2H_5$ group have a lower melting point than the straight-chain substance (Example 1).

Table 3

Example substances of the formula (IV)

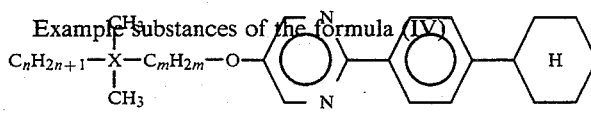

5-(alkyldimethyl(silyl)alkoxy)-2-(4''-alkyl-trans-cyclohexane-4'-phenyl)pyrimidine

| Example No. | n | x | m | p | $S_x$ | $S_c$ | $S_A$ | N | I |
|---|---|---|---|---|---|---|---|---|---|
| 8 | 4 | Si | 4 | 5 | 52 | (48) | — | | 87 |
| 9 | 4 | Si | 4 | 3 | 46 | 60 | — | | 100 |
| 10 | 4 | C | 6 | 3 | 48 | — | 85 | | 117 |

It can be seen from the compounds in Table 3 that, of the butyldimethyl-branched compounds, those containing a hexyloxy spacer are preferred since they have an $S_c$ phase instead of a phase of higher order, and they have a relatively high clearing point.

Comparison of Example Compound 8 with Example Compound 1 from Table 1 shows that the introduction of a dimethyl-branched group results in a depression in the melting point of 31° C.

In addition, these tricyclic compounds also have very low melting points in comparison with other dimethyl-branched tricyclic compounds. Thus, the compound described in DE-A 3 827 600 (see Example 57, 4-(5-(4-butyldimethylsilyl)butoxypyrimidin-2-yl)phenyl 5-trans-pentycyclohexanecarboxylate, which differs from the Example Compound 8 according to the invention only in that it contains an additional carboxyl group, has a melting point which is 30° C. higher.

We claim:

1. A ferroelectric liquid-crystalline mixture, which comprises from 0.1 to 25 mol-% of at least one cyclohexylphenylpyrimidine of the formula (I)

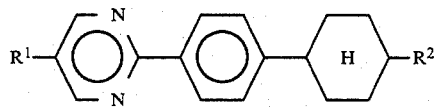 (I)

in which

R¹ is straight-chain or branched, chiral or achiral alkyl or alkenyl having 2 to 16 carbon atoms, in which one or two nonadjacent —CH₂— groups may be replaced by —O—, —S—, —CO—, —COO—, —OCO—, —Si(CH₃)₂— or —C(CH₃)₂—, and in which one or more hydrogen atoms of the alkyl or alkenyl radical may also be replaced by fluorine atoms, and in which the terminal CH₃ group of the alkyl may also be replaced by

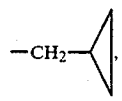

R² is straight-chain or branched, chiral or achiral alkyl having 1 to 10 carbon atoms.

2. The ferroelectric liquid-crystalline mixture as claimed in claim 1, wherein, in the formula (I),
R¹ is straight-chain or branched, chiral or achiral alkyl having 2 to 16 carbon atoms in which one —CH₂— group has been replaced by —C(CH₃)₂— or —Si(CH₃)₂— and in which a —CH₂— group which is nonadjacent thereto may be replaced by —O—, —S—, —COO— or —OCO—.

3. The ferroelectric liquid-crystalline mixture as claimed in claim 1, wherein, in the formula (I),
R¹ is straight-chain or branched, chiral or achiral alkyl having 2 to 16 carbon atoms in which the terminal CH₃ group has been replaced by

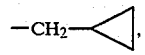

and in which one —CH₂— group may be replaced by —O—, —S—, —COO—, or —O—CO—.

4. The ferroelectric liquid-crystalline mixture as claimed in claim 1, wherein, in the formula (I),
R¹ is straight-chain alkyl having 4 to 12 carbon atoms in which one —CH₂— group may be replaced by —O— or —S—.

5. The ferroelectric liquid-crystalline mixture as claimed in claim 1, wherein, in the formula (I),
R¹ is straight-chain alkyl having 4 to 12 carbon atoms in which one —CH₂— group has been replaced by —C(CH₃)₂— and a further —CH₂— group which is nonadjacent thereto may be replaced by —O—.

6. The ferroelectric liquid-crystalline mixture as claimed in claim 1, wherein, in the formula (I),
R¹ is straight-chain alkyl having 4 to 12 carbon atoms in which the terminal CH₃ group has been replaced by

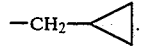

7. The ferroelectric liquid-crystalline mixture as claimed in claim 1, wherein, in the formula (I),
R² is straight-chain alkyl having 2 to 8 carbon atoms.

8. The ferroelectric liquid-crystalline mixture as claimed in claim 1, comprising at least 2 to 20 components.

9. The ferroelectric liquid-crystalline mixture as claimed in claim 1, comprising from 0.1 to 70 mol.-% of at least one cyclohexylphenylpyrimidine of the formula (I).

10. A ferroelectric switching and display device containing outer plates, electrodes, at least one polarizer, and a liquid-crystalline medium, wherein the liquid-crystalline medium is a ferroelectric liquid-crystalline mixture as claimed in claim 1.

11. A ferroelectric switching and display device as defined in claim 10 further containing an alignment layer.

* * * * *